United States Patent [19]

Person

[11] 4,097,507
[45] Jun. 27, 1978

[54] PROCESS FOR SEPARATING STRAIGHT AND BRANCHED CHAIN SOAPS AND THEIR ACIDS

[75] Inventor: Lucien Person, Levallois Perret, France

[73] Assignee: Produits Chimiques Ugine Kuhlmann, Paris, France

[21] Appl. No.: 754,964

[22] Filed: Dec. 28, 1976

[30] Foreign Application Priority Data

Jan. 13, 1976 France ............................... 76 00680

[51] Int. Cl.$^2$ ............................................. C11C 1/00
[52] U.S. Cl. ..................................... 260/413; 560/248
[58] Field of Search ................... 260/413 S, 417, 418, 260/419, 425; 560/248

[56] References Cited

U.S. PATENT DOCUMENTS 2,878,274  3/1959  Van Akkeren et al. ......... 260/425 X
3,678,097  7/1972  Puhk .................................. 260/410.6
3,983,147  9/1976  Senda et al. ...................... 260/418 X

FOREIGN PATENT DOCUMENTS 829,296  1/1952  Germany ............................. 260/418

*Primary Examiner*—Winston A. Douglas
*Assistant Examiner*—John F. Niebling
*Attorney, Agent, or Firm*—Pennie & Edmonds

[57] ABSTRACT

The present invention relates to a process for separating straight and branched chain soaps and their acids comprising adding to a solution of said soaps a water-soluble lithium compound in at least an amount stoichiometrically sufficient to convert the straight chain soaps present into the corresponding lithium salts, separating such lithium salts from such solution, treating such salts to recover straight chain organic acids and a lithium salt, and recovering branched chain organic acids from the solution.

8 Claims, No Drawings

PROCESS FOR SEPARATING STRAIGHT AND BRANCHED CHAIN SOAPS AND THEIR ACIDS

BACKGROUND OF THE INVENTION

The hydroformulation of straight chain olefins produces a mixture of straight chain aldehydes and branched chain aldehydes. Oxidation of these aldehydes or the corresponding alcohols inevitably produces a mixture of straight chain acids and branched chain acids or even the salts of these acids, more specifically the soaps. Each of these soaps, whether prepared by hydroformylation of olefins followed by oxidation or by some other process, possesses characteristic properties which often differ considerably one from the other. In contrast to straight chain soaps, branched chain soaps do not possess the properties of natural soap. Accordingly, it is especially important to separate the straight chain soaps and branched chain soaps from each other so that the characteristics of each type can be used to the best advantage for specific applications.

Known processes for separating the straight chain soaps, the branched chain soaps and their acids include fractional crystallization at low temperatures, or employing the differing solubility of the complexes formed with urea, or the differing solubility of certain of their salts in a solvent medium. These processes are extremely complicated and do not provide perfect results.

German Pat. No. 829,296 describes a process for separating straight chain acids in mixtures containing isomeric acids by the precipitation in an aqueous or non-aqueous medium of the alkaline earth salts or heavy metal salts of the straight chain acids. Separation of the heavy metal salts of straight chain acids by precipitation in aqueous media produces an imperfect separation. Separation of the alkaline earth salts of straight chain acids by precipitation in aqueous media necessitates long and difficult filtration of a colloidal precipitate.

In German Pat. No. 829,296 the alkaline salts of straight chain acids are not important to the separation process as the differences in solubility with respect to the alkaline salts of the branched chain acids are too minor.

SUMMARY OF THE INVENTION

It has now been found that, although the alkaline salts of straight chain acids as a whole cannot be effectively separated from branched chain alkaline salts, the lithium salts of straight chained acids constitute an exception. The lithium salts of straight chain soaps are in the form of crystals which can be readily separated by filtration or centrifugation.

Briefly stated, the present invention comprises a process for separating straight and branched chain soaps and their acids comprising adding to a solution thereof a water-soluble lithium compound in at least an amount stoichiometrically sufficient to convert the straight chain soaps into the corresponding lithium salts, separating said lithium salts from said solution, treating said salts to recover straight chain organic acids and a lithium salt, and recovering branched chain organic acids from said solution.

DETAILED DESCRIPTION

The claimed process is generally applicable to mixtures of straight and branched chain soaps. However, it is particularly applicable to soap mixtures containing 8 to 22 carbon atoms in their molecule and most suitable $C_{15}$ to $C_{18}$ soaps. These soap mixtures are generally in the form of potassium or sodium salts of such acids.

The lithium compound must be added in a water-soluble form such as a hydroxide, halide, sulfate, nitrate, organic acid salt, or the like and preferably as a salt of a strong acid in an aqueous solution. Lithium sulfate and lithium chloride are preferred. The quantity of the soluble lithium compound to be employed preferably corresponds to at least the stoichiometric amount of the straight chain soaps to be converted into a lithium salt. However, an excess of the lithium compound does not constitute a disadvantage in terms of the quality of the subsequent separations process as branched chain lithium salts are soluble in water.

The reaction temperature is not critical in the process according to the invention. Generally, the reaction takes place at a temperature lower than the boiling point of the aqueous solution of the soap mixture. The temperature can be such that the addition of the soluble lithium compound to the aqueous solution containing the mixture of soluble soaps of straight chain acids and branchedchain acids produces the immediate formation of the straight chain lithium soap precipitate.

In a preferred embodiment of the invention the addition of the soluble lithium compound to the aqueous solution containing the mixture of soluble soaps of straight and branched chain acids takes place at a temperature at which the linear chain lithium soaps are still soluble in the branched chain soap solution. After cooling the solution to ambient temperature the straight chain lithium soaps crystallize producing crystals which can easily be separated by conventional filtration or centrifugation techniques.

After precipitation or crystallization of the lithium salt of the straight chain acids, they are separated from the aqueous solution containing the soluble soaps of the branched chain acids by filtration or centrifugation. The separation process takes place as indicated hereinafter. The action of a powerful acid, such as sulfuric or hydrochloric, according to known and conventional procedures, firstly on the lithium salts, releases the straight chain organic acids and forms a lithium salt of such acid which can be recycled for repeated use. Secondly, the action of the strong acid on the salt remaining in the aqueous solution makes it possible to obtain the branched chain organic acids.

The present invention is designed to permit efficient separation of the straight chain soaps from the branched chain soaps and, consequently, to prepare extremely pure straight chain acids and branched chain acids. Straight chain soaps and acids have similar properties and applications to those of natural saturated soaps and acids. Branched chain sodium soaps have an improved wetting capacity over thse of straight chain sodium soaps whereas their foaming capacity is less than that of straight chain sodium soaps.

The following examples are given to illustrate the best modes for carrying out the present invention, but are not to be construed as restricting the scope thereof.

EXAMPLE 1

600 grams of a mixture of straight and branched chain sodium soaps synthesized from $C_{15}$ to $C_{18}$ olefins and containing 74% branched chain acids and 26% straight chain acids are dissolved in 9 liters of water at 50° C. 618 ml. of a solution containing 53 grams lithium sulfate are gradually added in the course of 15 minutes to the solution prepared in the above manner. A precipitate forms as the solution continues to be added. Upon completion of the addition, the temperature is 47° C. After cooling at ambient temperature the precipitate is filtered on a standard Buchner funnel (diameter 25 cm.) and thereafter washed with water. The washing water is added to the filtrate.

The filtrate is acidified with sulfuric acid so as to release the organic acids. After decanting, washing and drying, 349 grams of an acid mixture containing 94% branched chain acids is otained.

The precipitate is dispersed in 500 ml. of water and thereafter the mixture is heated to 60° C. and acidified with 6 N. sulfuric acid. The released organic acids which are kept at approximately 60° C. are decanted, washed and dried. 136 grams of acid containing 98% straight chain acids is obtained. The aqueous portion containing lithium sulfate is recycled for repeated use.

EXAMPLE 2

600 grams of a mixture of straight and branched chain sodium soaps synthesized from $C_{15}$ to $C_{18}$ olefins and containing 74% branched chain acids and 26% straight chain acids are dissolved in 9 liters of water at 70° C. 618 ml. of a solution containing 52 grams lithium sulfate are added to the solution prepared in the above manner and the temperature maintained at 70° C. Precipitation does not take place, but by allowing the solution to cool to ambient temperature crystallization of lithium soap takes place. After cooling to ambient temperature the crystals are separated from the solution by filtration on a Buchner (diameter 25 cm.). Filtration is rapid and takes 20 minutes.

The solution is acidified with sulfuric acid to release the organic acids. After decanting, washing and drying, 340 grams of acid containing 95% branched chain acids is obtained.

The crystals are dispersed in 500 ml. of water and thereafter the mixture is heated to 60° and acidified with 6 N. sulfuric acid. The released organic acids which are kept at approximately 60° C. are decanted, washed and dried. 135 grams of acid containing 99% straight chain acids is obtained. The lithium sulfate contained in the aqueous portion is recycled for repeated use.

EXAMPLE 3

600 grams of a mixture of straight and branched chain sodium soaps produced from $C_{15}$ to $C_{18}$ olefins and containing 75% branched chain acids and 26% straight chain acids are dissolved in 6 liters of water at 50° C.

When the solution is treated as described in Example 1, 360 g. of acid containing 93% branched chain acids and 130 grams of acid containing 97% straight chain acids are obtained.

EXAMPLE 4

30 grams of a mixture of straight and branched chain sodium soaps synthesized from $C_{11}$ to $C_{14}$ olefins and containing 58% branched chain acids and 42% straight chain acids are dissolved in 100 ml. water. 35 ml. of a solution containing 2.95 grams lithium sulfate are added at ambient temperature to the solution prepared in the above manner. The precipitate forms as the solution is added. The precipitate is thereafter filtered on the Buchner and washed.

The filtrate is acidified with sulfuric acid to release the organic acids. After decanting, washing and drying, 15 grams of acid containing 85% branched chain acids is obtained.

The precipitate dispersed in water is acidified with 6 N. sulfuric acid. The released organic acids which are kept at approximately 60° C. are decanted, washed and dried. 11 grams of acid containing 95% straight chain acids is obtained. The lithium sulfate contained in the aqueous portion is recycled.

EXAMPLE 5

30 grams of a sodium soap mixture prepared from $C_{11}$ to $C_{14}$ olefins are dissolved in 100 ml. water. 35 ml. of a solution containing 2.95 grams lithium sulfate are added to this solution which is brought to 70° C. Precipitation does not take place but cooling to ambient temperature produces the formation of lithium soap crystals.

The crystals are separated from the solution by filtration.

By treating the solution and crystals as described in Example 2, 17.9 grams of acid containing 81% branched chain acids and 8.5 grams of acid containing 98% straight chain acids are obtained.

EXAMPLE 6

20 grams of a sodium soap mixture prepared from $C_{11}$ to $C_{14}$ olefins are dissolved in 100 ml. water. 24 ml. of a solution containing 2 grams lithium sulfate are added to this solution which is brought to a temperature of 70° C. Cooling to ambient temperature causes formation of lithium soap crystals. The crystals are separated from the solution by filtration.

By treating the solution and crystals as described in Example 2, 11.8 grams of acid containing 80% branched chain acids and 6.8 grams of acid containing 95% straight chain acids are obtained.

EXAMPLE 7

45 grams of a sodium soap mixture prepared from $C_8$ and $C_{10}$ olefins containing 73% straight chain soaps and 27% branched chain soaps are dissolved in 60 ml. water at 70° C. 54 ml. of solution containing 9 grams lithium sulfate are added to this solution and the temperature is maintained at 70° C. After the solution has been added, cooling at ambient temperature produces formation of lithium soap crystals. The crystals are separated from the solution by filtration.

By treating the solution and crystals as described in Example 2, 20 grams of acid containing 53% branched chain acids and 19.5 grams of acid containing 98% straight chain acids are obtained.

EXAMPLE 8

11 grams of a sodium soap mixture prepared from $C_8$ and $C_{10}$ olefins are dissolved in 100 ml. water. 27 ml. of solution containing 2.3 grams lithium sulfate are added to the solution which is kept at 70° C. After the solution has been added, cooling to 10° C. produces the formation of lithium soap crystals. The crystals are separated from the solution by filtration.

By treating the solution and the crystals as described in Example 2, 4.5 g. of acid containing 60% branched chain acids and 5 grams of acid containing 98% straight chain acids are obtained.

EXAMPLE 9

400 grams of a mixture of straight and branched chain sodium soaps synthetized from $C_{15}$ to $C_{18}$ olefins and containing 74% branched chain acids and 26% straight chain acids are dissolved in 9 liters of water at 70° C.

400 ml. of a solution containing 26 grams lithium chloride are added to the solution prepared in the above-described manner while maintaining the temperature at 70° C. After cooling at ambient temperature the crystals formed during cooling are separated from the solution by filtration on a Buchner.

The solution is acidified with hydrochloric acid to release the organic acids. After decanting, washing and drying, 235 grams of acid containing 94% branched chain acids is obtained.

The crystals are dispersed in 300 ml. of water and the mixture is thereafter heated to 70° and acidified with hydrochloric acid. The released organic acids are decanted, washed and dried. 85 grams of acid containing 99% straight chain acids is obtained. The lithium chloride containing in the aqueous portion is recycled for repeated use.

EXAMPLE 10

100 grams of a mixture of straight chain and branched chain potassium soaps synthesized from $C_{15}$ to $C_{18}$ olefins and containing 74% branched chain acids and 26% straight chain acids are dissolved in 1.2 liters water at 70° C. 100 ml. of a solution containing 8 grams of lithium sulfate are added to the solution prepared in the above manner while maintaining the temperature at 70° C. After cooling at ambient temperature the crystals formed during cooling are separated from the solution by filtration on a Buchner.

The solution is acidified with sulfuric acid to release the organic acids. After decanting, washing and drying, 54 grams of acid containing 95% branched chain acids is obtained.

The crystals are dispersed in 60 ml. of water and the mixture thereafter heated to 60° C. and acidified with sulfuric acid.

The organic acids which are released are decanted, washed and dried. 21 grams of acid containing 99% straight chain acids is obtained.

The lithium sulfate contained in the aqueous portion is recycled for repeated use.

While the invention has been described in connection with the preferred embodiments, it is not intended to limit the ivnention to the particular forms set forth, but, on the contrary, it is intended to cover such alternatives, modifications, and equivalents as may be included within the spirit and scope of the invention as defined by the appended claims.

What is claimed is:

1. A process for separating straight and branched chain soaps comprising adding to a solution thereof a water-soluble lithium compound selected from a hydroxide, halide, sulfate, nitrate, and organic acid salt in at least an amount stoichiometrically sufficient to convert the straight chain soaps into the corresponding lithium salts, separating said lithium salts as a precipitate from said solution, acidifying said salts to recover straight chain organic acids and a lithium salt, and recovering branched chain organic acids from said solution.

2. The process of claim 1 wherein the lithium compound is added in the form of an aqueous solution.

3. The process of claim 1 wherein the lithium compound is the lithium salt of a strong acid.

4. The process of claim 1 wherein the solution of soaps is at a temperature lower than its boiling point and the lithium compound is added to the soap solution at a temperature above the temperature at which the straight chain lithium salts are soluble in the solution.

5. A process for separating $C_8$ to $C_{22}$ straight and branched chain soaps from aqueous solutions thereof comprising adding to said solution a lithium salt selected from lithium sulfate, lithium chloride, or mixtures thereof in an amount stoichiometrically sufficient to convert the straight chain soaps into the corresponding lithium salts, forming said corresponding lithium salts into a precipitate, separating said precipitate from said solution, acidifying said precipitate with a strong acid to generate a lithium salt of said strong acid and straight chain organic acids, and acidifying the solution remaining after separation of the lithium salt precipitate with a strong acid to form the branched chain organic acids.

6. The process of claim 5 wherein the temperature of the aqueous soap solution is below the boiling point of said solution and the lithium salt is added to said aqueous solution in the form of an aqueous solution and a temperature at which the straight chain lithium salts are still soluble in said aqueous soap solution.

7. The process of claim 5 wherein the aqueous soap solution is that resulting from the oxidation of mixtures of straight and branched chain aldehydes produced by the hydroformylation of straight chain olefins.

8. The process of claim 5 wherein the strong acid used to acidify is sulfuric acid.

* * * * *